US012758702B2

(12) United States Patent
Ho et al.

(10) Patent No.: US 12,758,702 B2
(45) Date of Patent: Oct. 13, 2026

(54) INFUSION PUMPS AND METHODS WITH SHAPE MEMORY WIRE DRIVEN SYRINGE MECHANISM

(71) Applicant: Tandem Diabetes Care, Inc., San Diego, CA (US)

(72) Inventors: Eduardo Ho, San Diego, CA (US); Reza Farshchi, San Diego, CA (US); William T. Trevaskis, San Marcos, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 719 days.

(21) Appl. No.: 18/090,788

(22) Filed: Dec. 29, 2022

(65) Prior Publication Data

US 2023/0201452 A1 Jun. 29, 2023

Related U.S. Application Data

(60) Provisional application No. 63/294,651, filed on Dec. 29, 2021.

(51) Int. Cl.
*A61M 5/142* (2006.01)
*A61M 5/168* (2006.01)

(52) U.S. Cl.
CPC .... *A61M 5/14248* (2013.01); *A61M 5/16804* (2013.01); *A61M 2205/0266* (2013.01)

(58) Field of Classification Search
CPC .......... A61M 5/14248; A61M 5/14254; A61M 2005/14268; A61M 2005/14506; A61M 2205/0266
See application file for complete search history.

(56) References Cited

U.S. PATENT DOCUMENTS

| | | | |
|---|---|---|---|
| 4,529,401 | A | 7/1985 | Leslie et al. |
| 4,723,947 | A | 2/1988 | Konopka |
| 5,084,021 | A | 1/1992 | Baldwin |
| 5,135,491 | A | 8/1992 | Baldwin |
| 5,176,502 | A | 1/1993 | Sanderson et al. |
| 5,232,449 | A | 8/1993 | Stern et al. |
| 5,259,732 | A | 11/1993 | Stern |
| 5,261,884 | A | 11/1993 | Stern et al. |

(Continued)

FOREIGN PATENT DOCUMENTS

| | | |
|---|---|---|
| CA | 2597024 | 10/2006 |
| CA | 2 932 976 A1 | 2/2012 |

(Continued)

OTHER PUBLICATIONS

International Search Report and Written Opinion for Application No. PCT/US2022/054247 mailed May 9, 2023.

(Continued)

*Primary Examiner* — Laura A Bouchelle
(74) *Attorney, Agent, or Firm* — Merchant & Gould P.C.

(57) ABSTRACT

Disclosed herein are apparatuses and methods for an ambulatory infusion pump actuated with a shape memory alloy (SMA) wire. An SMA wire operated mechanism can include an actuator lever to increase the SMA wire's strain into a usable displacement to move a pawl that ratchets to a ratchet wheel to rotate a lead screw to advance a plunger a precise amount within a reservoir to deliver a precise amount of fluid.

20 Claims, 15 Drawing Sheets

(56) References Cited

U.S. PATENT DOCUMENTS

| | | | |
|---|---|---|---|
| 5,295,966 | A | 3/1994 | Stern et al. |
| 5,334,162 | A | 8/1994 | Harris |
| 5,364,387 | A | 11/1994 | Sweeney |
| 5,478,316 | A | 12/1995 | Bitdinger et al. |
| 5,527,307 | A | 6/1996 | Srisathapat et al. |
| 5,582,591 | A | 12/1996 | Cheikh |
| 5,637,092 | A | 6/1997 | Shaw |
| 5,695,472 | A | 12/1997 | Wyrick |
| 5,755,696 | A | 5/1998 | Caizza |
| 5,832,971 | A | 11/1998 | Yale et al. |
| 5,887,793 | A | 3/1999 | Kieffer |
| 5,971,722 | A | 10/1999 | Maget et al. |
| 6,006,798 | A | 12/1999 | Lindquist |
| 6,200,296 | B1 | 3/2001 | Dibiasi et al. |
| 6,254,569 | B1 | 7/2001 | O'Donnell et al. |
| 6,500,150 | B1 | 12/2002 | Gross et al. |
| 6,656,159 | B2 | 12/2003 | Flaherty |
| 6,699,218 | B2 | 3/2004 | Flaherty et al. |
| 6,716,190 | B1 | 4/2004 | Glines et al. |
| 6,802,828 | B2 | 10/2004 | Reynolds |
| 6,843,782 | B2 | 1/2005 | Gross et al. |
| 6,971,999 | B2 | 12/2005 | Py et al. |
| 7,018,361 | B2 | 3/2006 | Gillespie, Jr. et al. |
| 7,081,105 | B2 | 7/2006 | Reilly et al. |
| 7,108,679 | B2 | 9/2006 | Alchas |
| 7,740,607 | B2 | 6/2010 | Willis et al. |
| 7,972,303 | B2 | 7/2011 | Caizza et al. |
| 8,012,132 | B2 | 9/2011 | Lum et al. |
| 8,573,027 | B2 | 11/2013 | Rosinko et al. |
| 8,821,440 | B2 | 9/2014 | Sanchez et al. |
| 9,173,998 | B2 | 11/2015 | Rosinko et al. |
| 9,180,243 | B2 | 11/2015 | Michaud |
| 9,421,329 | B2 | 8/2016 | Kruse |
| 9,452,255 | B2 | 9/2016 | Tieck et al. |
| 9,555,186 | B2 | 1/2017 | Kruse |
| 9,750,897 | B2 | 9/2017 | Alchas |
| 10,279,107 | B2 | 5/2019 | Michaud |
| 10,434,253 | B2 | 10/2019 | DiPerna et al. |
| 10,729,847 | B2 | 8/2020 | Gray et al. |
| 11,458,246 | B2 | 10/2022 | Seitz et al. |
| 11,776,671 | B2 | 10/2023 | Blumberg, Jr. et al. |
| 2003/0005926 | A1 | 1/2003 | Jones et al. |
| 2004/0153032 | A1 * | 8/2004 | Garribotto ........ A61M 5/14248 604/131 |
| 2007/0276329 | A1 | 11/2007 | Mernoe |
| 2013/0053816 | A1 | 2/2013 | DiPerna et al. |
| 2017/0246383 | A1 | 8/2017 | Lanier, Jr. et al. |
| 2023/0047034 | A1 | 2/2023 | Michaud |

FOREIGN PATENT DOCUMENTS

| | | | | |
|---|---|---|---|---|
| CN | 107469186 | | 8/2019 | |
| CN | 110691618 | A | 1/2020 | |
| DE | 692 33 602 | T2 | 12/2006 | |
| EP | 1 987 855 | A2 | 11/2008 | |
| EP | 1987855 | | 9/2012 | |
| EP | 1 513 573 | B1 | 7/2013 | |
| EP | 2 630 980 | A1 | 8/2013 | |
| EP | 2211939 | B1 | 12/2018 | |
| JP | 3304585 | B2 | 7/2002 | |
| JP | 2005-533545 | A | 11/2005 | |
| JP | 4357611 | B2 | 11/2009 | |
| JP | 2019-536572 | A | 12/2019 | |
| KR | 10-2019-0023512 | A | 3/2019 | |
| RS | 20100326 | A2 | 4/2012 | |
| WO | 92/04063 | A1 | 3/1992 | |
| WO | 93/21974 | A1 | 11/1993 | |
| WO | 94/27660 | A1 | 12/1994 | |
| WO | 99/43282 | A1 | 9/1999 | |
| WO | 00/06228 | A1 | 2/2000 | |
| WO | WO-2005072795 | A2 * | 8/2005 | ........ A61M 5/14248 |
| WO | 2006/000785 | A1 | 1/2006 | |
| WO | 2006/020953 | A1 | 2/2006 | |
| WO | 2010/151265 | A1 | 12/2010 | |

OTHER PUBLICATIONS

European Supplementary Search Report for App. No. 22917352, mailed on Aug. 7, 2025, 21 pages.

* cited by examiner

INFUSION PUMPS AND METHODS WITH SHAPE MEMORY WIRE DRIVEN SYRINGE MECHANISM

RELATED APPLICATION

The present application claims the benefit of U.S. Provisional Application No. 63/294,651, filed Dec. 29, 2021, which is hereby incorporated herein in its entirety by reference.

TECHNICAL FIELD

The present disclosure relates generally to ambulatory infusion pumps and, more particularly, to a user-wearable pump, such as a patch pump, for delivering medicament such as insulin to a patient.

BACKGROUND

There are a wide variety of medical treatments that include the administration of a therapeutic fluid in precise, known amounts at predetermined intervals. Devices and methods exist that are directed to the delivery of such fluids, which may be liquids or gases, are known in the art. One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an injector pen. Such ambulatory infusion pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

One type of pump that has been developed is a patch pump, or micro pump. Patch pumps generally are small pumps, typically ambulatory, that are carried directly on the skin under the user's clothing. Many such pumps are situated directly on the infusion site such that no tubing is required to deliver the insulin and/or other medicament to the patient. Other patch pumps can be positioned on the patient's body with a short length of tubing extending to a nearby infusion site.

Some patch pumps can be at least in part disposable, meant to be worn for a period of time such as, e.g., a day or two, and then discarded and replaced by a new patch pump. Other patch pump designs contemplate a disposable component, such as a cartridge that contains medicament, and a reusable or durable component. In such configurations, the disposable and durable components may be joined together by the patient or caregiver in preparation for delivery of the medicament.

Ambulatory infusion pumps such as patch pumps can employ various actuation mechanisms for driving the system to deliver medicament to the user, including electromagnetic drive motors, piezoelectric motors, and electrically driven shape-memory alloy (SMA) wire actuators. SMA wire has been used in a variety of miniaturized mechanism designs, including patch pumps, and has cost and size advantages over other actuation mechanism. SMA wire actuators operate on the principle of material phase transformation due to electrical heating. This phase transformation generates an approximately 4% strain in the form of shrinkage that can be used to operate on a mechanism and extract usable work. One disadvantage of SMA technology is relatively low work and power output that makes it not suitable for applications that require high power or high work output. However, a disposable medical pump with low delivery rates is an example of a type of application for which SMA wire mechanisms would be suitable.

SUMMARY

Disclosed herein are apparatuses and methods for an ambulatory infusion pump actuated with a shape memory alloy (SMA) wire. An SMA wire operated mechanism can include an actuator lever to increase the SMA wire's strain into a usable displacement to pull on a pawl that ratchets to a ratchet wheel to rotate a lead screw to advance a plunger a precise amount within a reservoir to deliver a precise amount of fluid.

In an embodiment, an ambulatory infusion pump can include a reservoir configured to contain a medicament and a syringe assembly including a plunger configured to dispense medicament from the reservoir. A ratchet wheel configured to rotate the syringe assembly can be disposed on the syringe assembly and a pawl can be engaged with the ratchet wheel. An actuator lever can be mechanically linked to the pawl and a shape memory wire can be mechanically linked to the actuator lever. Actuation of the shape memory wire can shorten the shape memory wire to cause the shape memory wire to move the actuator lever such that the actuator lever moves the pawl to rotate the ratchet wheel and syringe assembly to cause the plunger to dispense a predetermined amount of medicament from the reservoir.

In an embodiment, an ambulatory infusion pump can include a reservoir configured to contain a medicament, a syringe assembly including a plunger configured to dispense medicament from the reservoir and a ratchet wheel and pawl mechanism mechanically linked to the syringe assembly. A shape memory wire can be mechanically linked with the ratchet and pawl mechanism such that actuation of the shape memory wire shortens the shape memory wire to cause the shape memory wire to move the pawl to rotate the ratchet wheel and syringe assembly to cause the plunger to dispense a predetermined amount of medicament from the reservoir.

The above summary is not intended to describe each illustrated embodiment or every implementation of the subject matter hereof. The figures and the detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which.

Figure 1A:
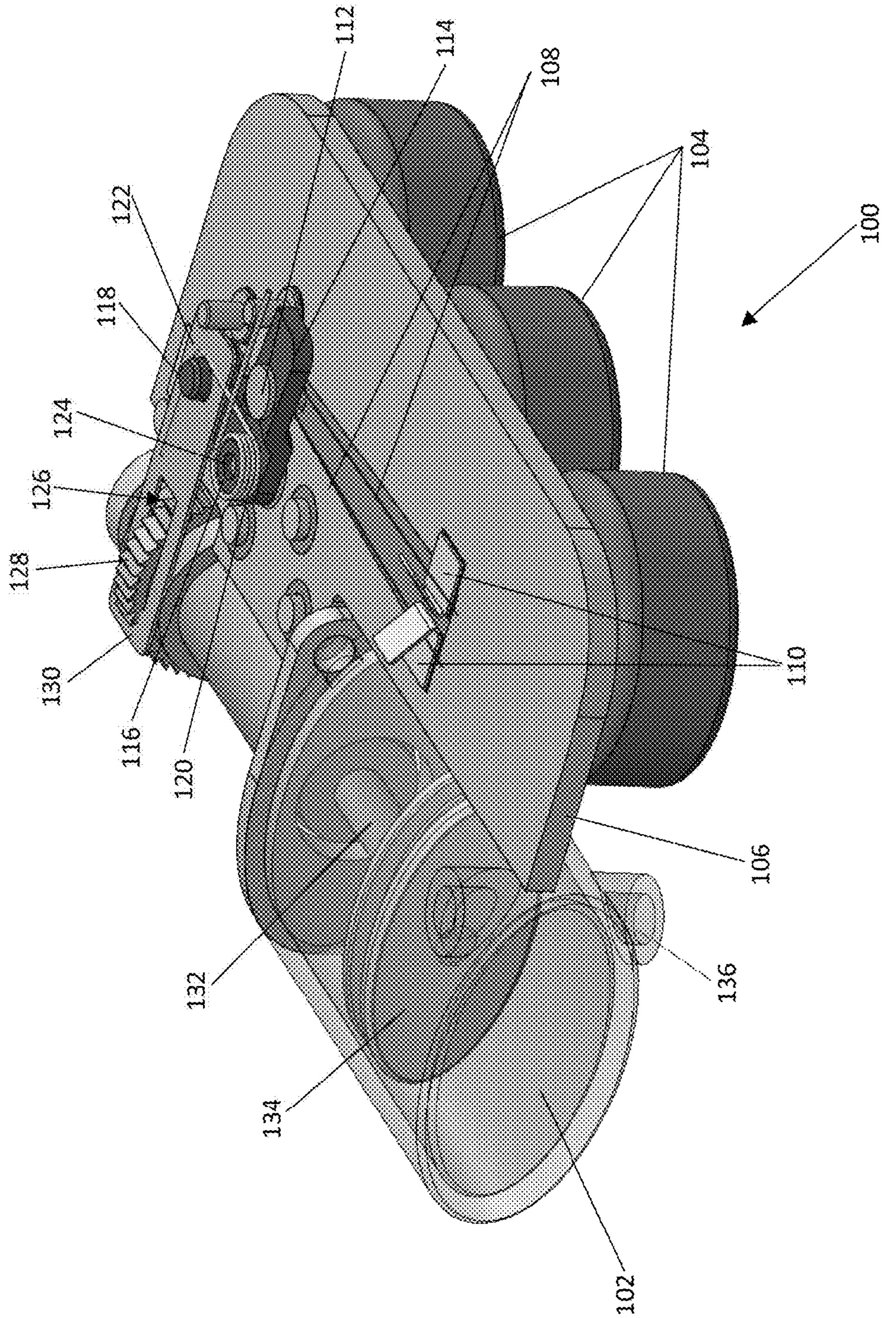
FIGS. 1A-1C depict various views of an infusion pump according to an embodiment of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1B:
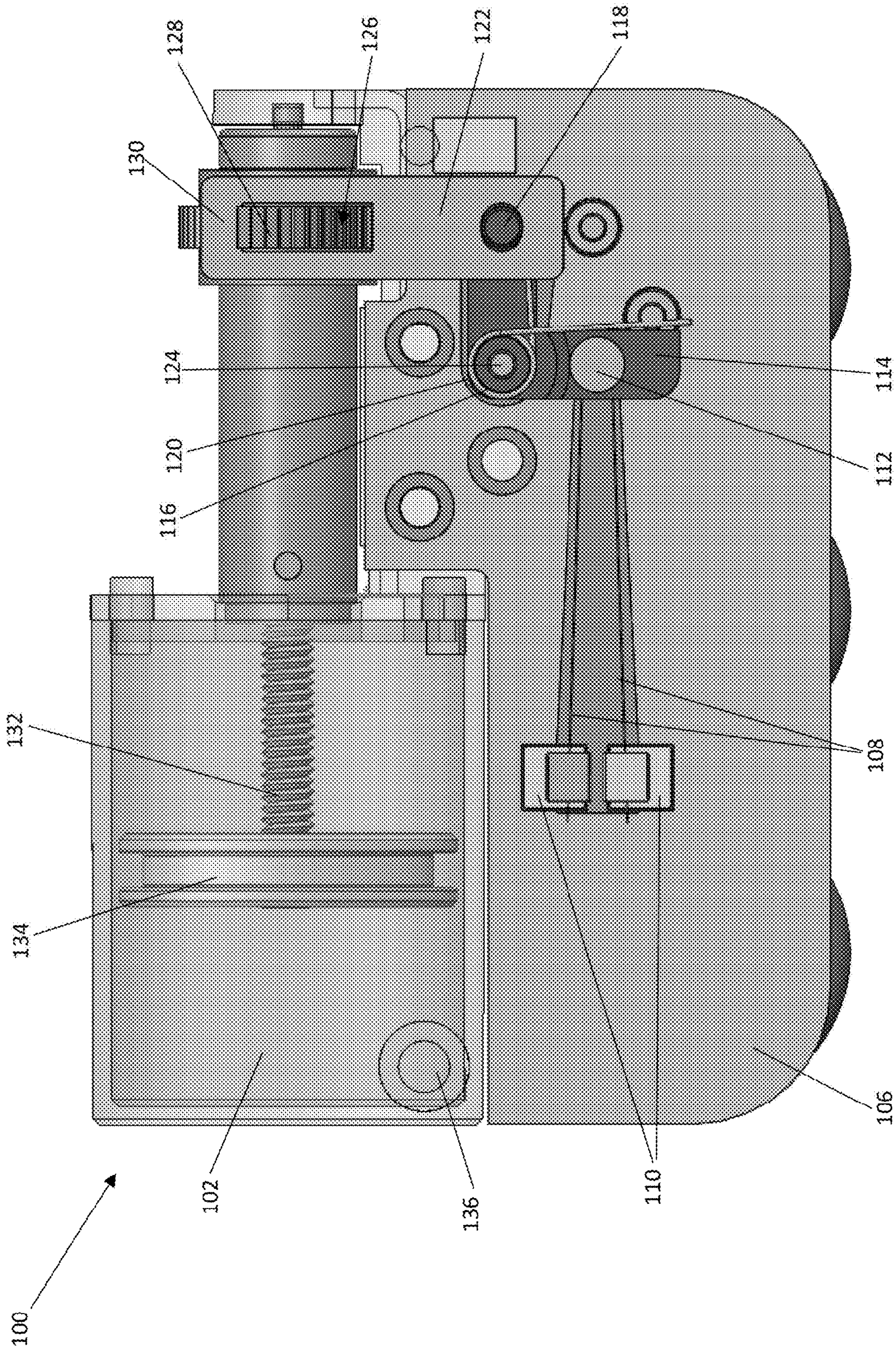
Figure 1C:
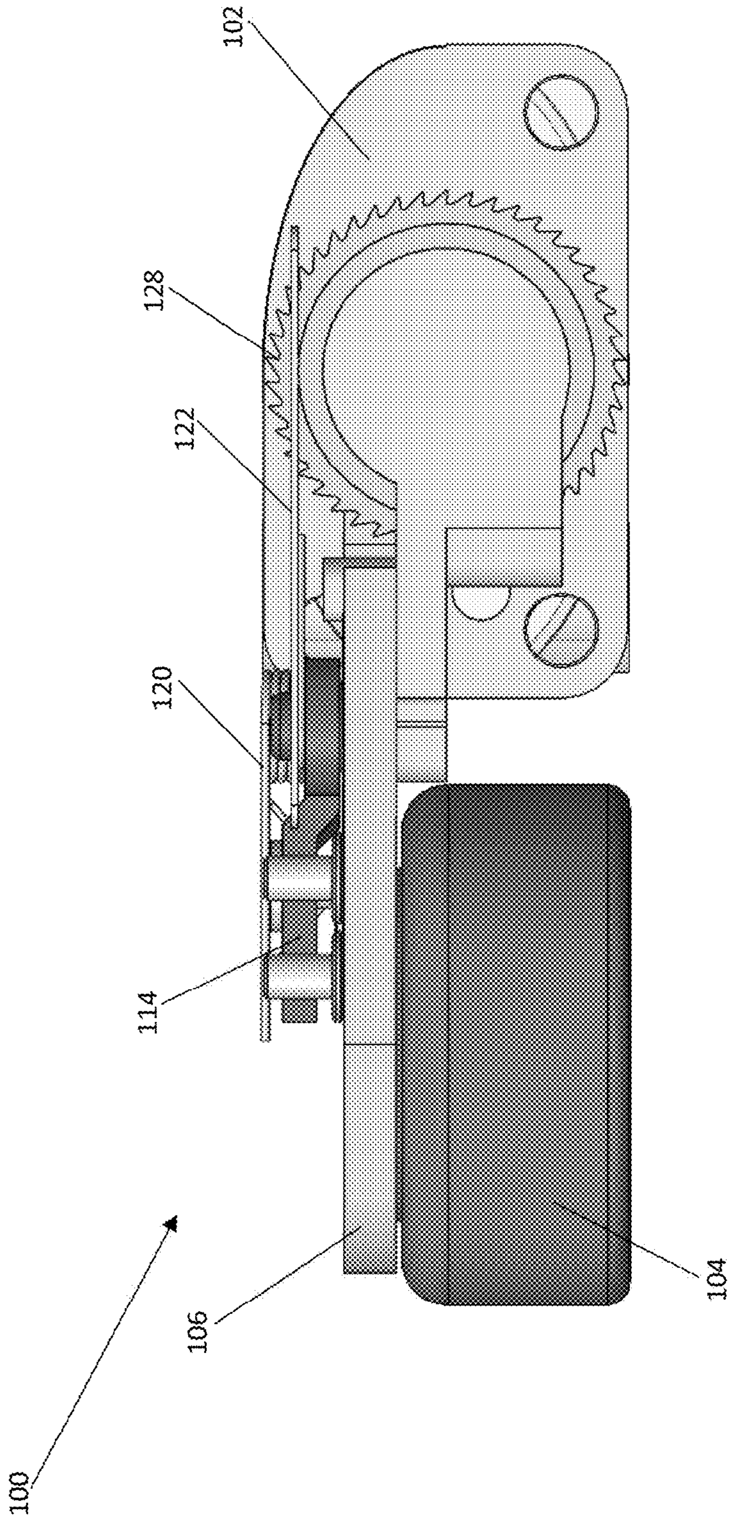

FIGS. 1A-1C depict a user-wearable infusion pump 100 that may be configured as a disposable patch pump according to the disclosure. Infusion pump 100 can include a housing (not pictured) surrounding the depicted components. A reservoir 102 can be configured to contain a medicament. In embodiments, infusion pump 100 can be a single use ambulatory pump intended to be worn directly on a user's body and disposed of after using the medicament in the reservoir 102. In some embodiments, the reservoir 102 can have a small volume, i.e., 1 mL or less, and be intended for use with concentrated insulin and/or for pediatric applications that have small delivery volumes. Such an infusion pump 100 can also include an adhesive patch (not pictured) that enables the user to wear the pump directly on the user's body. Infusion pump 100 can be powered by one or more coin cell batteries 104 disposed within housing. The components of the system can be mounted on a printed circuit board assembly (PCBA) 106 electrically connecting the battery with the other electronic components of the system. Pumps such as those disclosed herein can be actuated to give a consistent volume of fluid per electrical pulse at regular intervals such as every five minutes such that one or more pulses is required to deliver the desired volume of medicament each interval.

A shape memory alloy (SMA) wire 108, such as Nitinol, can extend from electrical connectors 110 and be routed around a pin 112. In embodiments, SMA wire 108 can be configured as a single continuous wire. Pin 112 can be mounted on assembly 108 in a manner that allows limited lateral movement of pin 112 and pin 112 can extend through an aperture in an actuator lever 114 with the pin 112 having a head that is larger than the aperture to prevent the actuator lever 114 from disengaging from pin 112. Actuator lever 114 can further include a first projection 116 for holding a spring 120 and a second projection 118 that extends through an aperture in a pawl 122. First projection 116 can be mounted on a rotation pin 124 that is rotatably fixed on the board 106 to enable the actuator lever 114 to be rotated about pin 124. Pawl 122 includes an elongate aperture 126 sized to fit around a portion of a ratchet wheel 128 and a distal surface 130 on which an individual tooth of the ratchet wheel can rest. As will be described in more detail below, rotation of ratchet wheel 128 drives a lead screw 132 to move a plunger 134 to deliver medicament contained in the reservoir 102 out an outlet 136.

Figure 2:
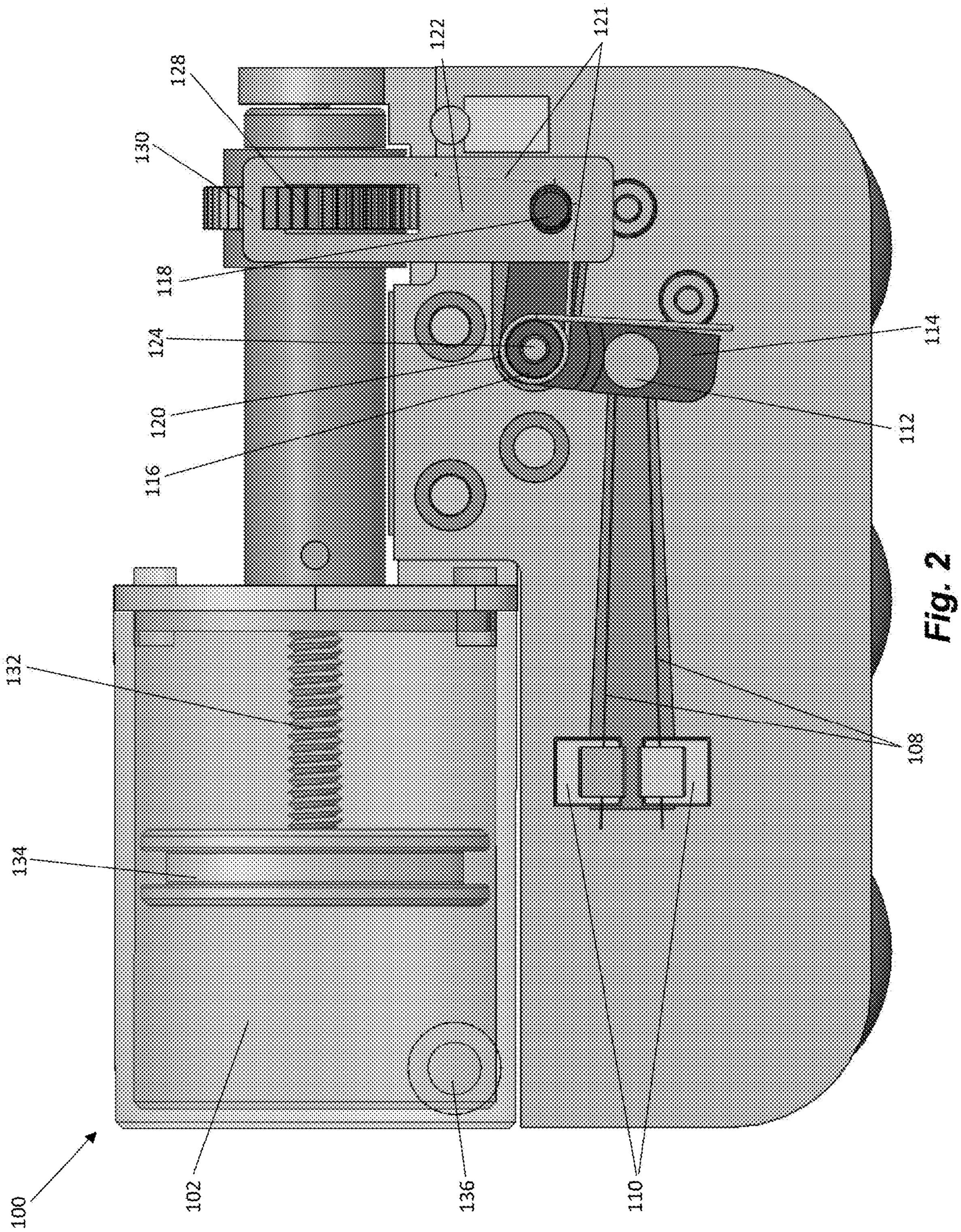
FIG. 2 depicts the infusion pump of FIGS. 1A-1C upon actuation.

Referring now to FIGS. 1B and 2, when SMA wire 108 is heated using energy from the batteries 104, the wire transitions from a first length to a second, shorter length. The shortening of the length of SMA wire 108 causes the wire to pull on the wire pin 112 it is wrapped around to move the pin 112 laterally towards the connectors 110 to which the SMA wire 108 is fixed (compare the position of pin 112 in FIG. 1B to the position in FIG. 2). The pin 112 therefore pulls on the actuator lever 114 to pivot the actuator lever about the rotation pin 124 through the first projection 116 of actuator lever. The second projection 118 of the actuator arm then also pulls on the pawl 122 causing the pawl 122 to pull on the ratchet wheel 128. As most clearly depicted in FIG. 1B, it can be seen that a distance between the rotation pin 124 about which the actuator lever 114 rotates and the connecting projection 118 attaching the actuator lever 114 to the pawl 122 is greater than a distance between the pivot pin 114 and the wire pin 112 around which the SMA wire wraps. This asymmetry enables the relatively small SMA-wire strain (i.e., change in length) to effectively be "multiplied" into a greater travel distance of the pawl 122 by the ratio of the distances between the two attachment pins 112, 118 and the pivot pin 114.

In embodiments, spring 120 is a torsion spring having an arm 121 that wraps around second projection 118 connecting the actuator lever 114 to the pawl 122. As such, following actuation of the SMA wire, when the wire returns to its original, longer length the biasing force of the arm 121 of the torsion spring 120 on the second projection 118 rotates the actuator lever 114 back about mounting pin 124 to return the pin 112 and second projection 118 to their original positions depicted in FIG. 1B. The dimensions, positioning, etc. of each of the components of the system can be configured such that with each such actuation the ratchet wheel 128 is rotated by a single tooth such that the next tooth on the wheel then rests on the distal end 130 of the pawl when the pawl 122 is moved back to its original position by the actuator lever 114. In addition, each single tooth rotation of the ratchet wheel 128 corresponds to a precise predefined amount of medicament that will be delivered from the reservoir 102. It has been found that, in some embodiments, by having the pawl 122 pull, rather than push, on the ratchet wheel 128 that the disclosed system is simpler, more robust, and less error prone that systems in which the pawl pushes a ratchet wheel.

Figure 3A:
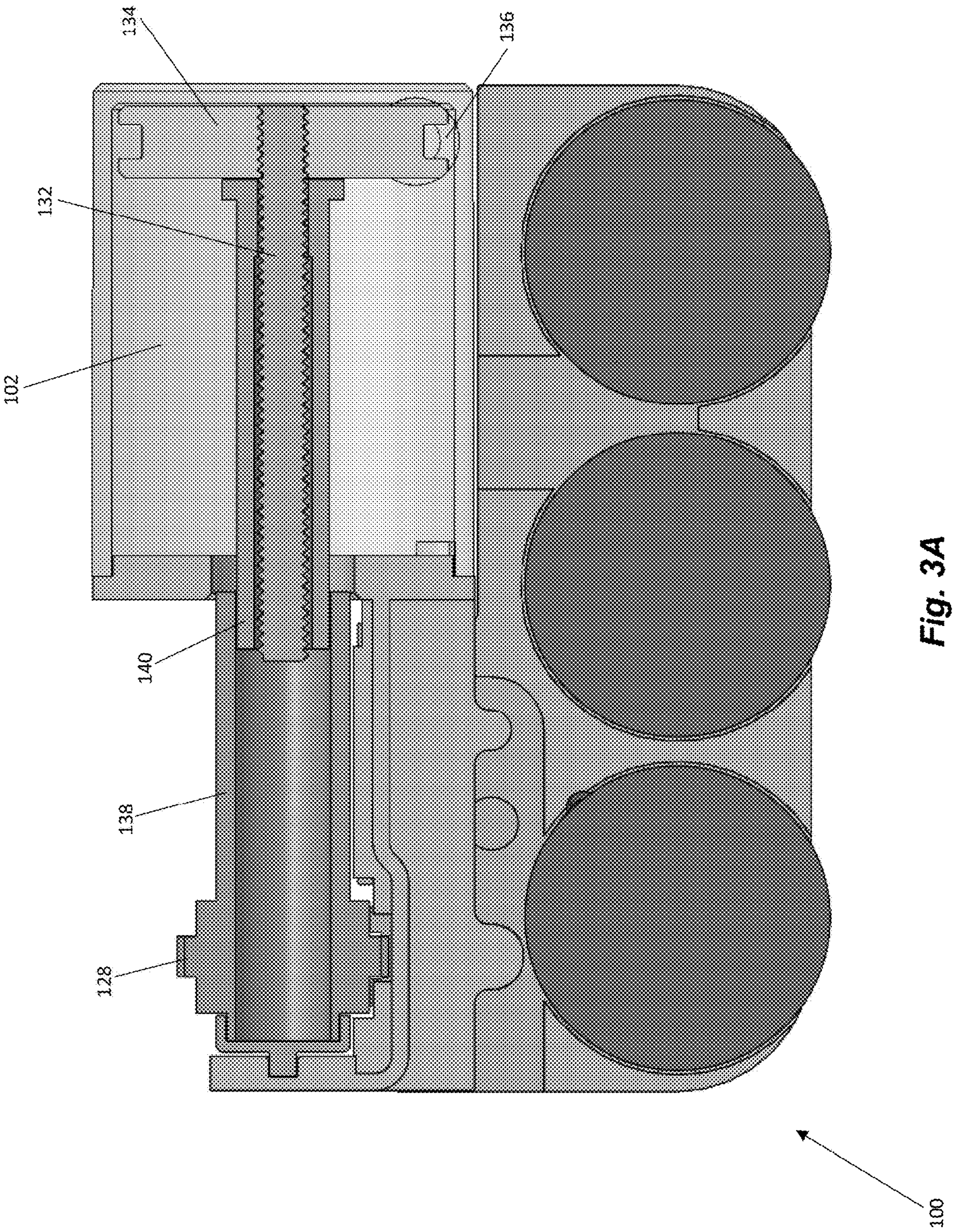
FIGS. 3A-3C depict cross-sectional views of the infusion pump of FIGS. 1A-1C.
Figure 3B:
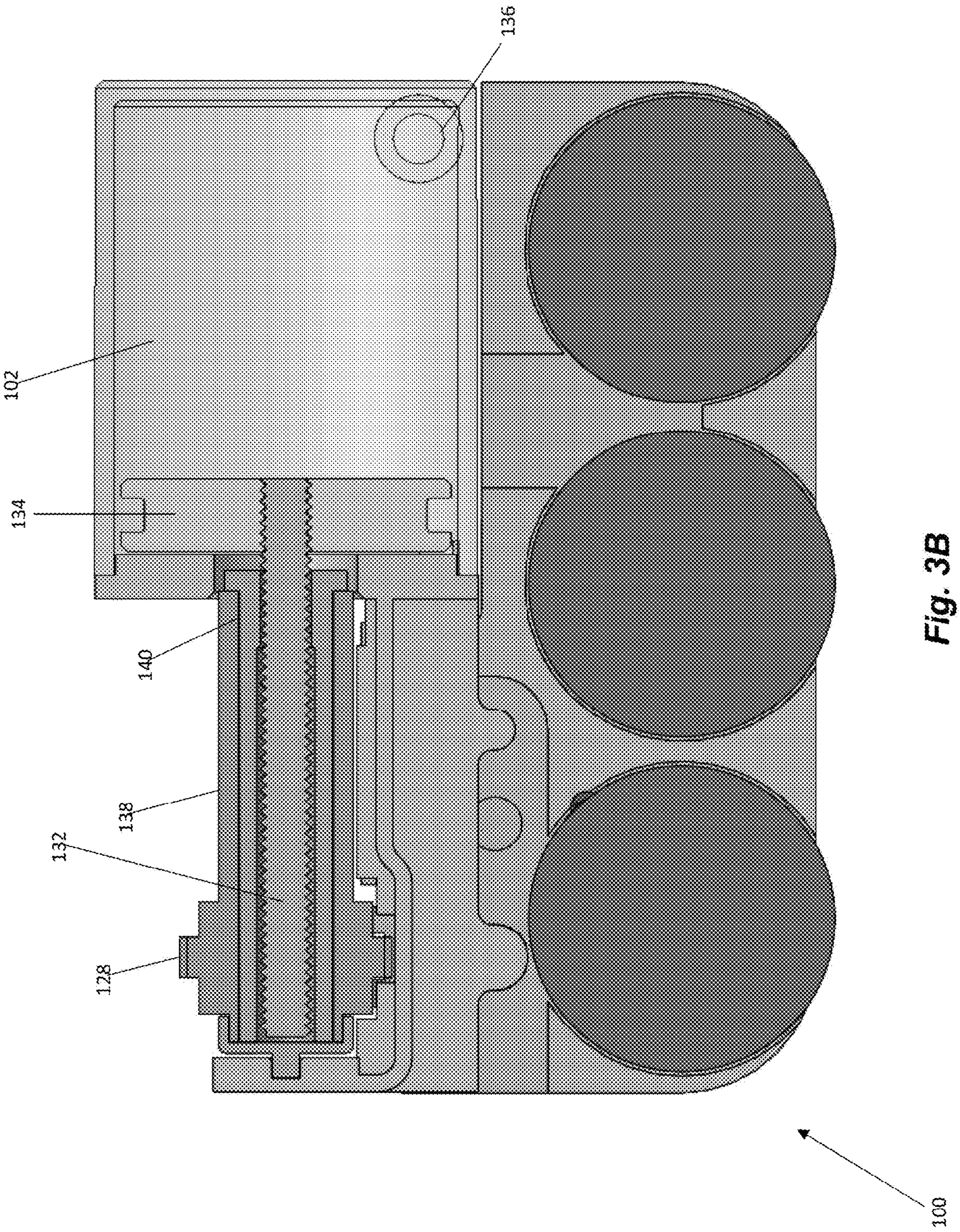
Figure 3C:
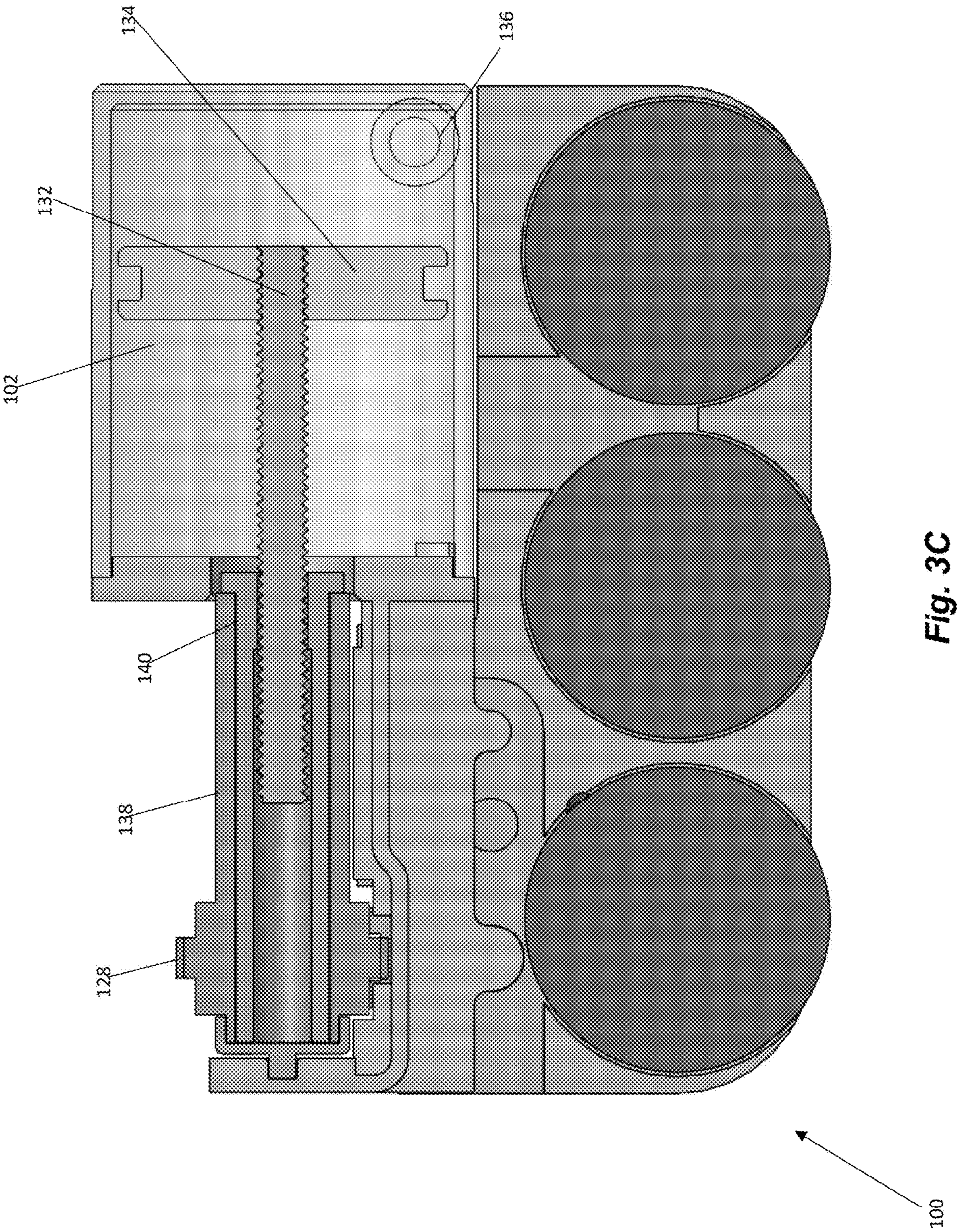

The manner in which rotation of the ratchet wheel 128 effects delivery of medicament with pump 100 can be described in greater detail with reference to FIGS. 3A-3C. Ratchet wheel 128 can be attached to or unitarily formed with a hollow tube 138 containing a drive tube 140 having a threaded interior that interfaces with the lead screw 132 attached to the plunger 134. Referring to FIG. 3A, the pump 100 is depicted in an empty, pre-filled configuration (i.e., because plunger 134 is at the distal end of reservoir 102 there can be no medicament in reservoir 102). When the pump is filled, as depicted in FIG. 3B, the drive tube 140 and lead screw 132 are fully nested inside of the hollow tube 138 with the plunger 134 at the far proximal end of the reservoir. As the device is incrementally operated to dispense medicament as described above, the lead screw 132 and plunger 134 are advanced distally through the reservoir 102 relative to the hollow tube 138 and drive tube 140 to force medicament out of the outlet 136 due to the threaded interior surface of the drive tube 140 driving the threaded lead screw 132 when the drive tube is rotated 140 by the interaction of the ratchet wheel 128 and pawl 122.

FIGS. 4A-4D depict the interior of a user-wearable infusion pump 200 according to another embodiment of the disclosure. Pump 200 operates using similar principles as pump 100 with a slightly different configuration. In this embodiment, the SMA wire 208 extends from connectors 210 and travels underneath pawl 222 to wrap around pin 212 attached to actuator lever 214. The actuator lever 214 is similarly configured to pivot about a pin 224 when pulled on by the SMA wire 208 to pull on the pawl 222 to which it is connected with a pin 218, projection, or other element. As with the previous embodiment, the pawl 222 then pulls on the ratchet wheel 228 to rotate the wheel to drive the lead screw 232 and plunger 234 to expel a precise amount medicament from the reservoir 202 corresponding to rotation of the ratchet wheel 228 by a single tooth. The actuator lever 214 can similarly be spring loaded such that when the SMA wire 208 is no longer electrically heated, and therefore cools off and elongates back to its original length, the actuator lever rotates back to its initial position depicted in FIG. 4A and the pawl resets onto the next tooth of the ratchet wheel 228. Referring to the partial view of FIG. 4C, it can be seen that a distance between the pivot pin 224 about which the actuator lever 214 rotates and the pin 218 attaching the actuator lever 214 to the pawl 222 is greater than a distance between the pivot pin 214 and the pin 212 around which the SMA wire wraps. This asymmetry enables the relatively small SMA-wire strain (i.e., change in length) to effectively be "multiplied" into a greater travel distance of the pawl 222 by the ratio of the distances between the two attachment pins 212, 218 and the pivot pin 214.

Figure 4A:
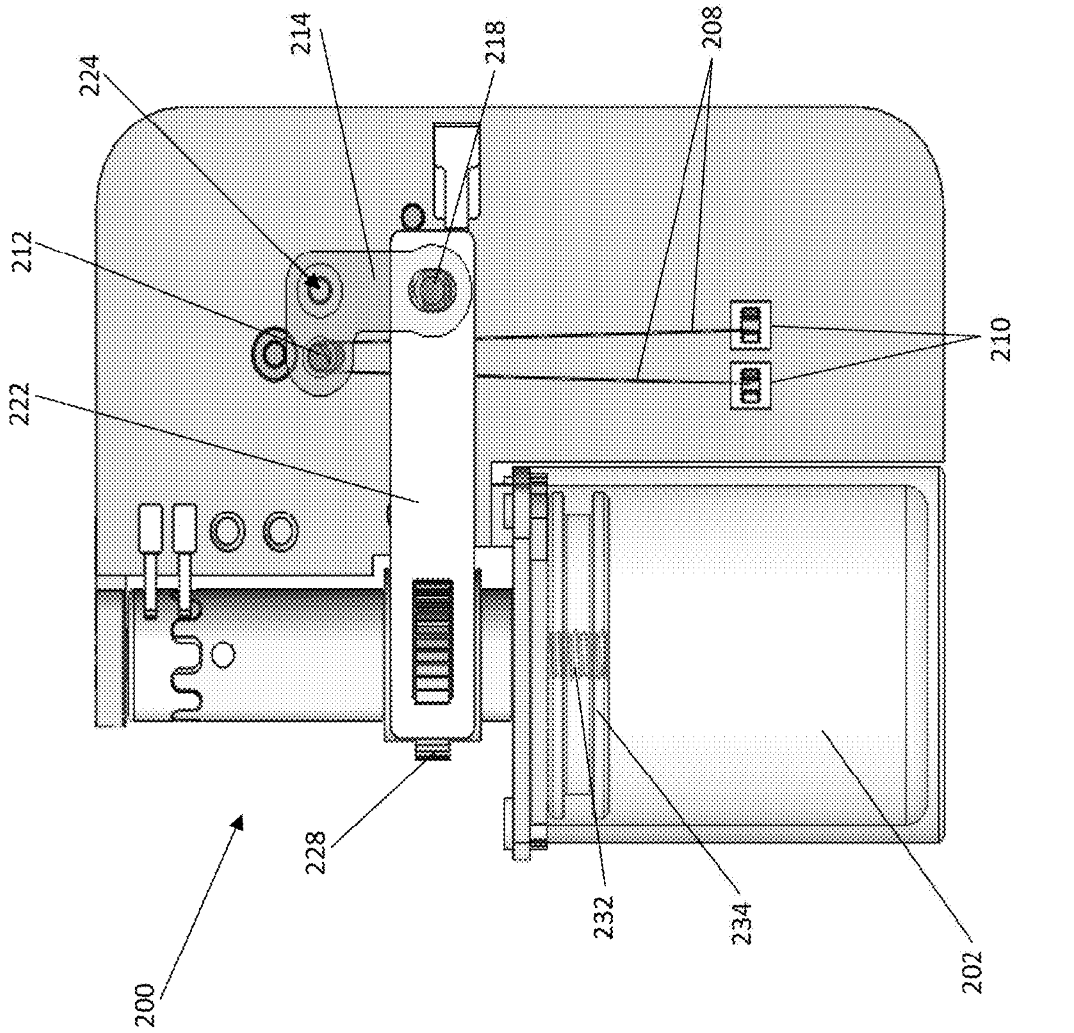
FIGS. 4A-4D depict various views of an infusion pump according to an embodiment of the disclosure.
Figure 4C:
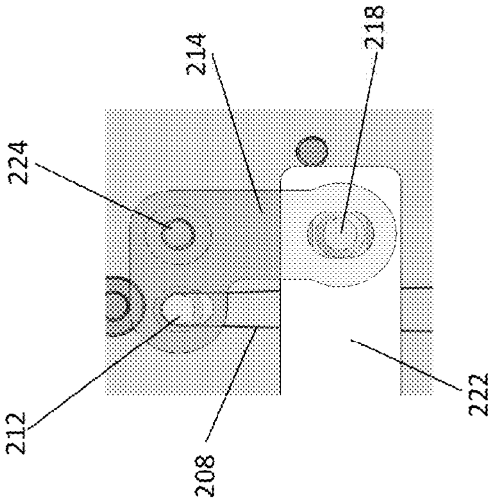
Figure 4B:
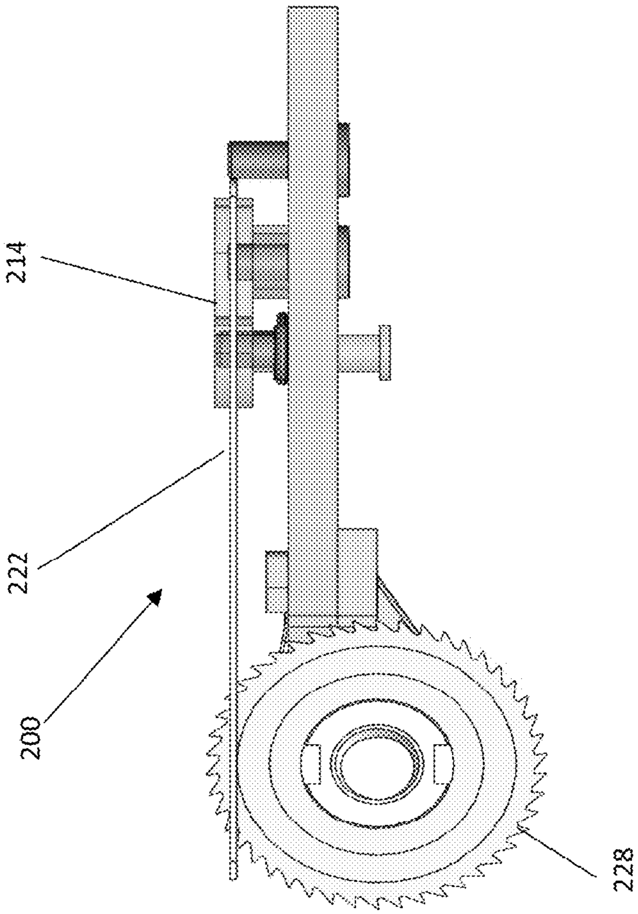
Figure 4D:
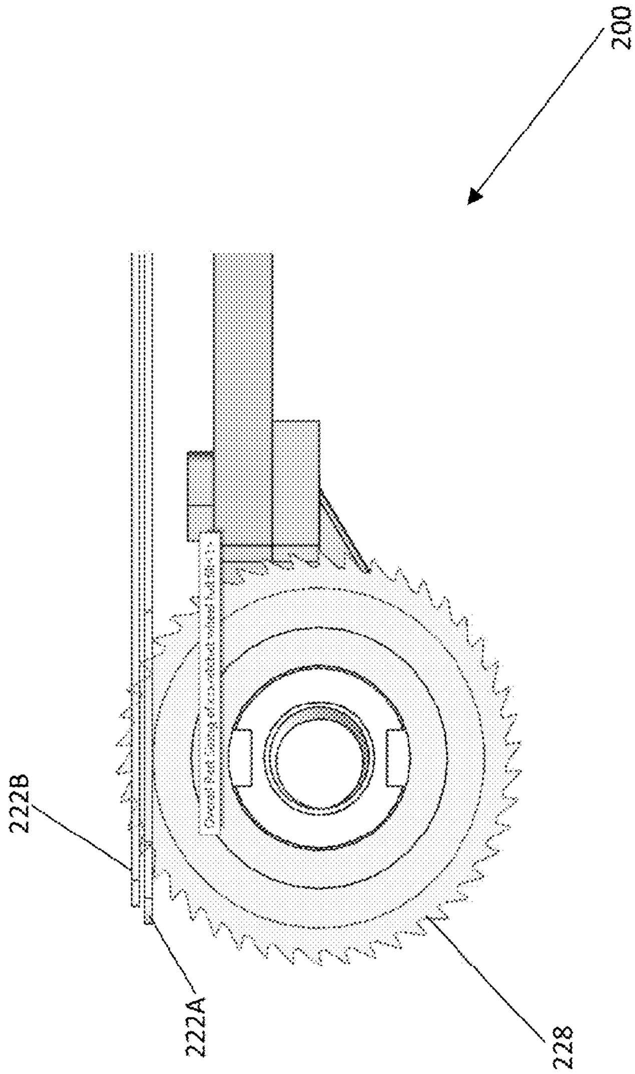

Referring now to FIG. 4D, the position of pawl 222 in both the "start" position 222A prior to actuation of the SMA wire and "finish" position 222B when the SMA wire has been actuated to move the pawl is depicted. As can be seen from these two positions, as the pawl 222 is pulled to actuate on the ratchet wheel 228 in response to the SMA wire being energized, the actuation radius of the pawl 222 to the center of the ratchet wheel 228 (i.e., a distance between the pawl and the center of the ratchet wheel) slightly increases such that progressively less force is required to rotate the wheel as the pawl moves. This reduces the effort felt by the SMA wire and helps increase the wire's longevity when actuating over many cycles because SMA alloys have a preference for having maximum stress at the beginning of the actuation and not at the end.

Figure 5:
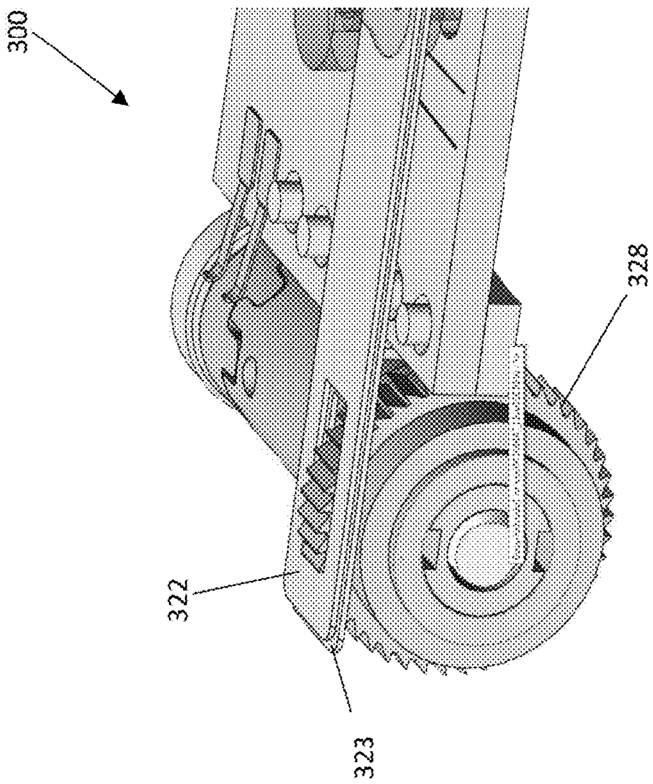
FIG. 5 depicts an infusion pump according to an embodiment of the disclosure.

FIG. 5 depicts the interior of a user-wearable infusion pump 300 according to another embodiment of the disclosure. Pump 300 operates using similar principles as pump 100, 200, but this embodiment includes two pawls 322, 323. In embodiments, the second pawl 323 can be offset from the first pawl 322 by a distance equivalent to half of a tooth of the ratchet wheel 328. Each pawl 322, 323 alternatively engages the ratchet wheel on each actuation of the SMA wire such that each actuation causes a half-tooth rotation of the ratchet wheel rather than a full tooth as in the previous embodiments. The result of this approach is to provide double the resolution (i.e., half the dose for each actuation) without modifying the size or pitch of the teeth on the ratchet wheel (which are already required to be manufactured very small). As such, a minimum dispense size of pump 300 is half that of pumps 100 and 200, assuming an otherwise equivalently sized system.

Figure 7A:
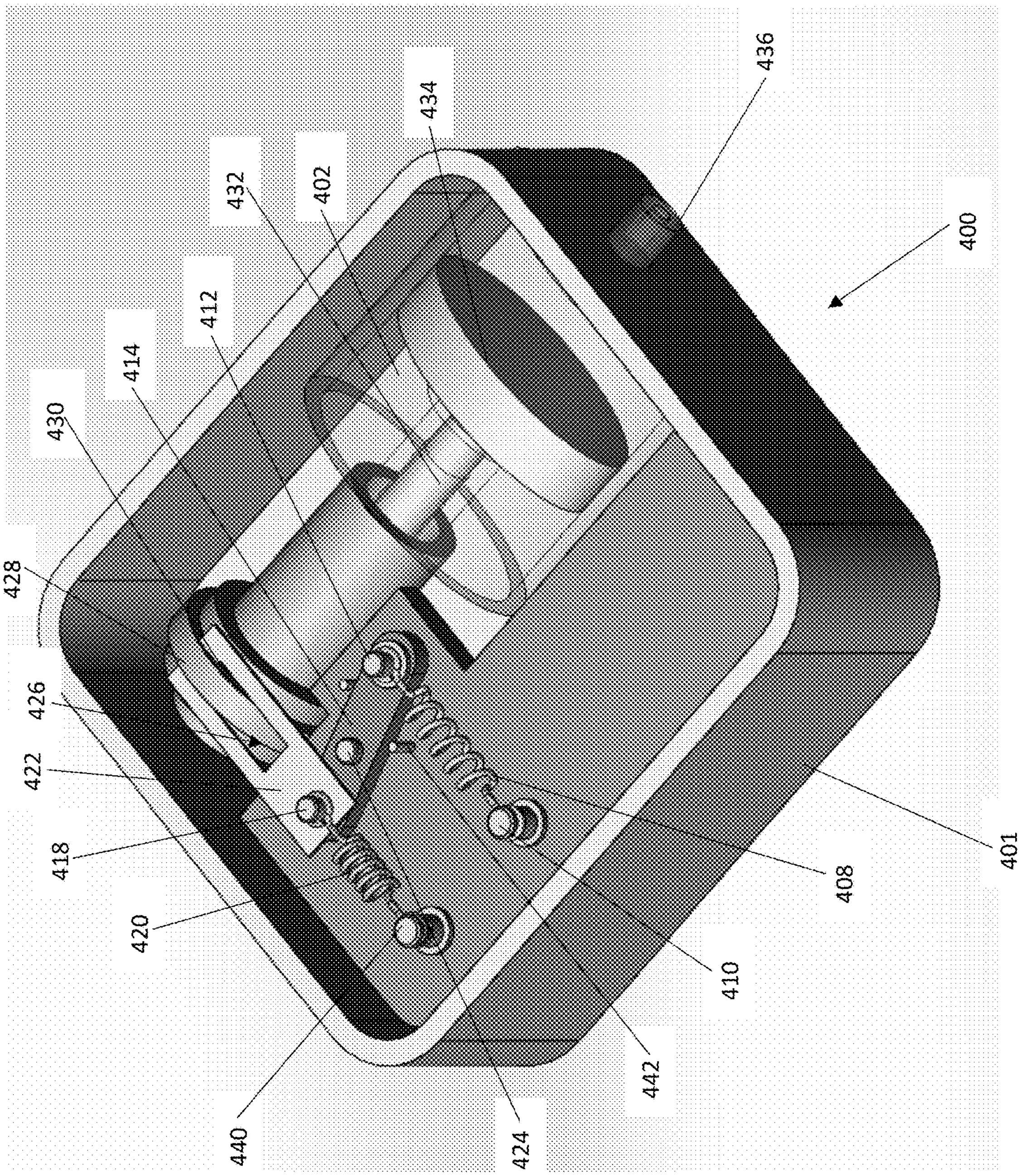
FIGS. 7A-7C depict an infusion pump according to an embodiment of the disclosure.
Figure 7B:
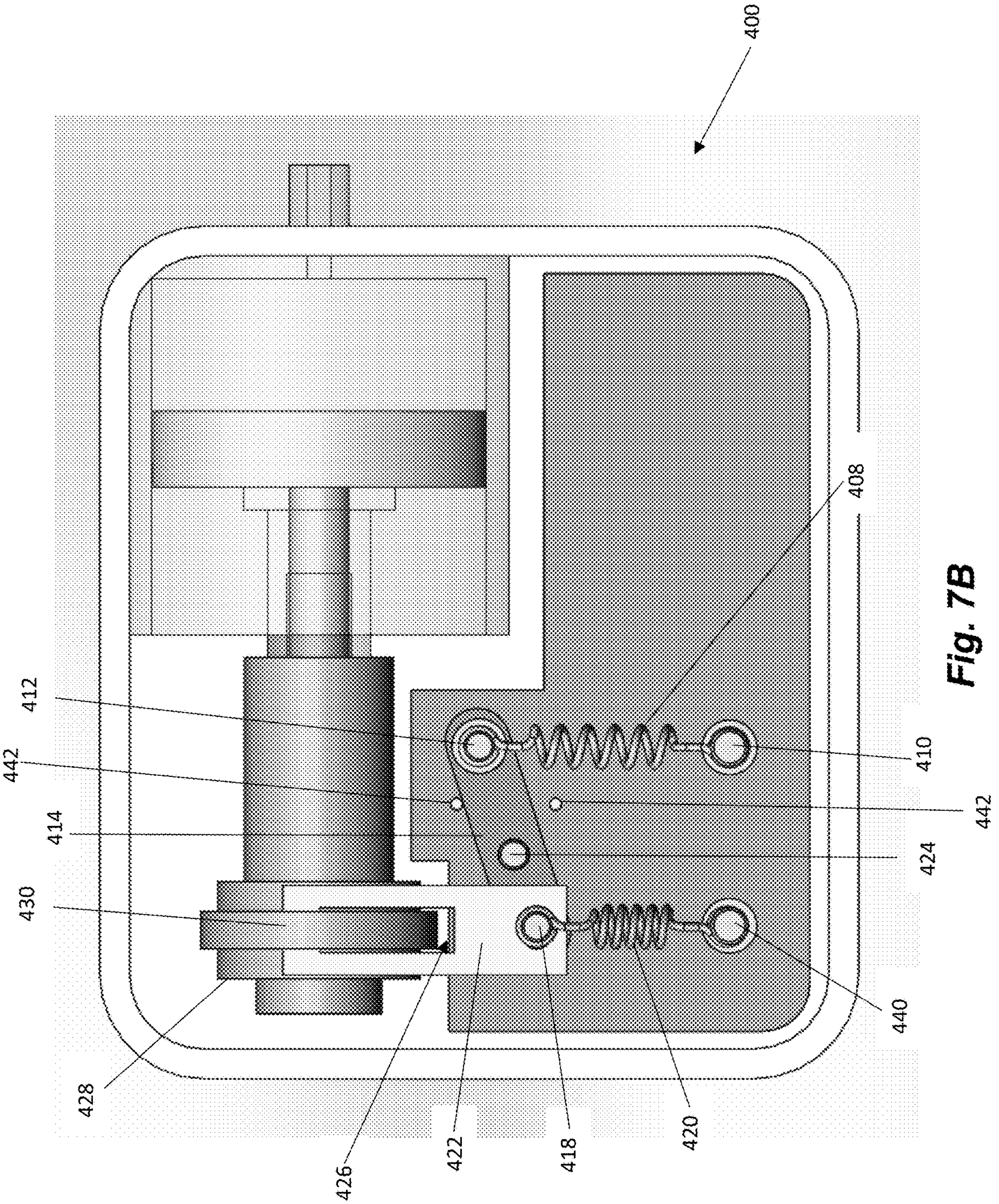
Figure 7C:
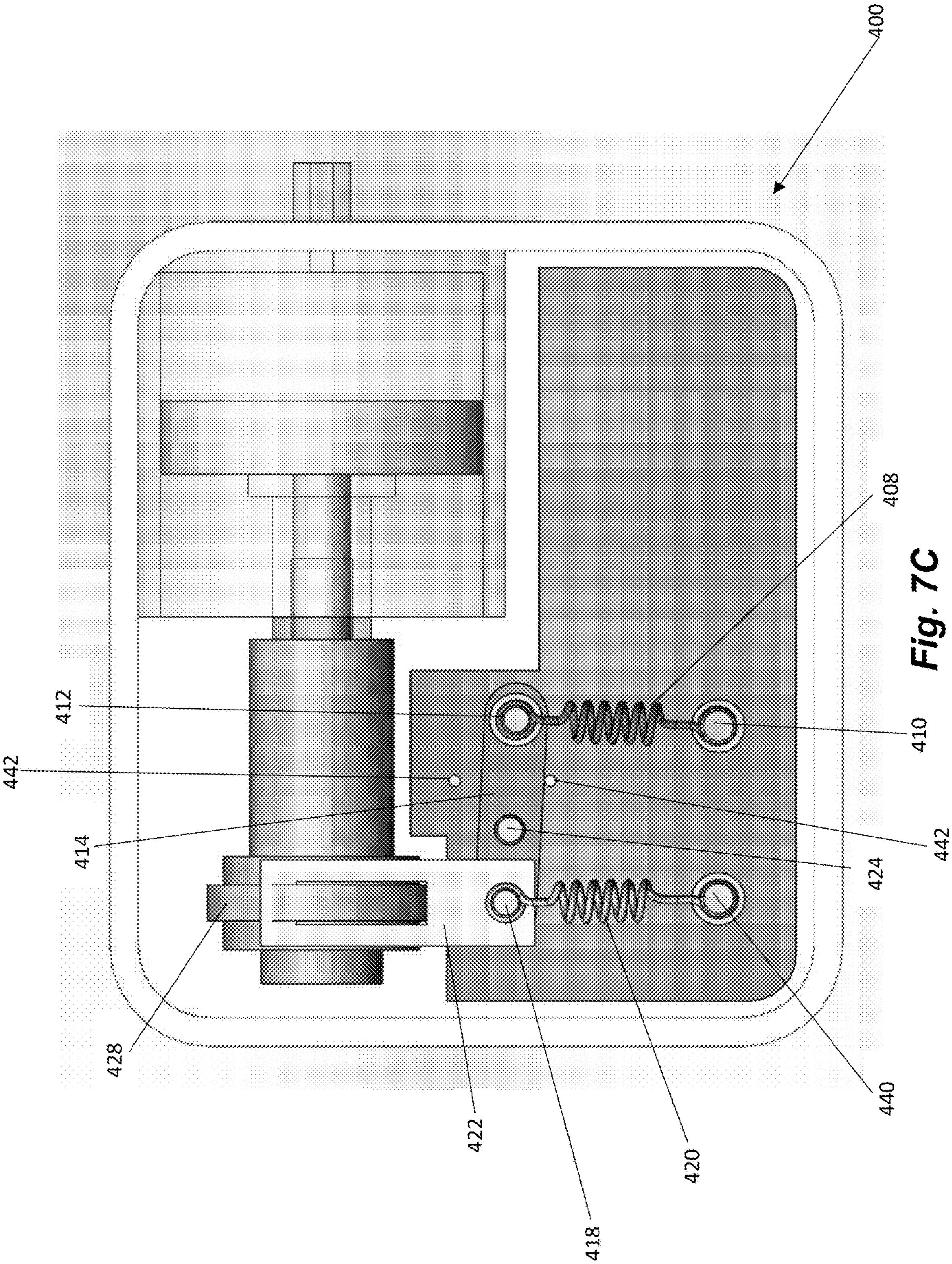

FIGS. 7A-7C depict an infusion pump 400 according to another embodiment of the disclosure. Pump 400 includes a number of similar components to those of pumps 100, 200, 300 including a reservoir 402, batteries (not depicted), PCBA (not depicted), SMA wire 408, electrical connector/pin 410, pin 412, actuator lever 414, spring 420, pawl 422, mounting pin 418, rotation pin 424 pawl aperture 426, ratchet wheel 428, distal surface 430 of pawl 422, lead screw 432, plunger 434 and outlet 436. Not depicted in the previous embodiments, though necessarily present, is a pump housing 401 surrounding the internal components.

In this embodiment, the SMA wire 408 is configured as a spring. The bias spring 420 extends from the same mounting pin 424 that connects the pawl 422 and the actuator lever 414 to another mounting pin 440 such that the bias spring 420 is aligned across from the SMA wire 408 along the actuator lever 414. As the actuator lever 414 pivots about the rotation pin 424, a pair of stop pins 442 are positioned on opposing sides of the actuator lever 414 adjacent the end to which the SMA wire 408 is attached to limit a path of travel of the actuator lever 414. This corresponds to how limiting how far the pawl 422 ("hot" state) and ratchet wheel 428 ("cold") state can travel, as will be apparent from the below.

FIG. 7B depicts the device 400 in the "cold" state in which the SMA wire 408 is not energized and therefore in an extended state. In this configuration, there is minimal force on the actuator lever 414. FIG. 7C depicts the device 400 in the "hot" state in which the SMA wire 408 is energized, which causes the SMA wire 408 to shorten and to therefore pull the pin 412 towards the electrical connector pin 410 to cause the actuator lever 414 to pivot about rotation pin 424. SMA wire 408 shortens with enough force to cause bias spring 420 to expand and move the side of the actuator lever 414 with the mounting pin 418 away from mounting pin 440. As pawl 422 is also attached to mounting pin 418, this movement therefore also pushes the pawl forwards along the ratchet wheel 428. Although not depicted herein, ratchet wheel will include teeth 428 similar to those depicted in the previous embodiments, and each actuation of the SMA wire 408 can cause the pawl 422 to advance the ratchet wheel 428 by a single tooth (or other predetermined number of teeth) to dispense a predetermined amount of medicament from the reservoir 402 as explained in more detail above. After the SMA wire 408 has been energized, it will gradually return to the "cold" state depicted in FIG. 7B. In this embodiment, rotation of the lead screw 432 to dispense medicament occurs as the SMA wire gradually returns from the "hot" state in FIG. 7C to the "cold" state of FIG. 7B. However, this approach can in other embodiments be reversed by exchanging the positions of the SMA wire spring 408 and the bias spring 420 such that the SMA wire spring is attached to the mounting pint 418 with the pawl 422 and the bias spring is on the opposite side of the lever actuator.

Figure 6B:
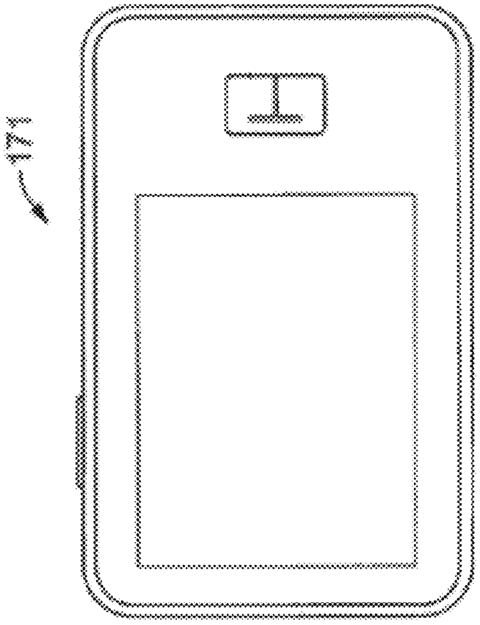
FIGS. 6A-6B depict one or more remote control devices that can be used to communicate with infusion pumps according to the disclosure.
Figure 6A:
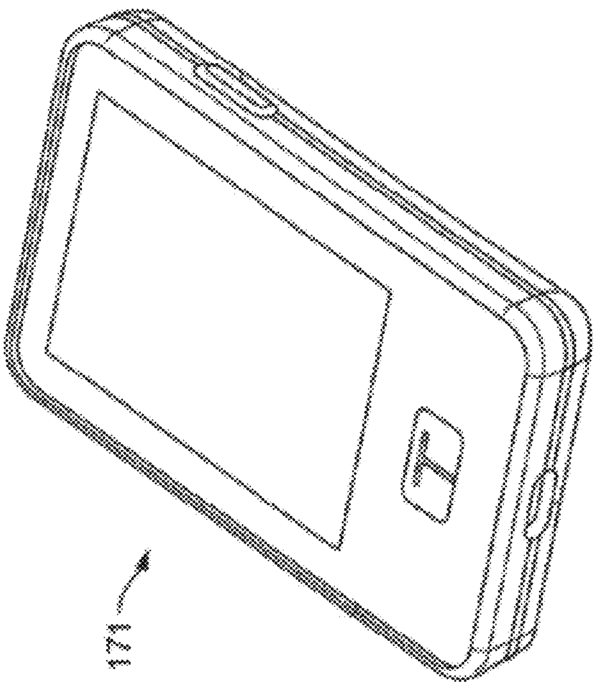

Referring to FIGS. 6A-6B, one or more remote control devices 170, 171 can be used to communicate with the processor of pump 100 to control delivery of medicament and transfer data with pump 100 via a wired or a wireless electromagnetic signal, such as via, e.g., a near field communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device, such as a smart phone (not depicted) executing a software application for control of the pump, a dedicated remote controller 171 (as depicted in FIGS. 4A-4B), a wearable electronic watch or electronic health or fitness monitor or personal digital assistant (PDA), etc., or a tablet, laptop or personal computer. Such communications between (and among) the one or more remote control devices and pump 100 may be one-way or two-way for, e.g., effective transfer of data among the devices and the pump, control of pump operations, updating software on the devices and/or pump, and allowing pump-related data to be viewed on the devices and/or pump.

In embodiments, an ambulatory infusion pump can include a reservoir configured to contain a medicament and a syringe assembly including a plunger configured to dispense medicament from the reservoir. A ratchet wheel configured to rotate the syringe assembly can be disposed on the syringe assembly and a pawl can be engaged with the ratchet wheel. An actuator lever can be mechanically linked to the pawl and a shape memory wire can be mechanically linked to the actuator lever. Actuation of the shape memory wire can shorten the shape memory wire to cause the shape memory wire to move the actuator lever such that the actuator lever moves the pawl to rotate the ratchet wheel and syringe assembly to cause the plunger to dispense a predetermined amount of medicament from the reservoir.

In some embodiments, the actuator lever pulls on the pawl to rotate the ratchet wheel and syringe assembly when the shape memory wire is actuated.

In some embodiments, the actuator lever pushes on the pawl to rotate the ratchet wheel and syringe assembly when the shape memory wire is actuated.

In some embodiments, the ratchet wheel comprises a plurality of teeth and a distance between each tooth corresponds to the predetermined amount of medicament.

In some embodiments, each actuation of the shape memory wire causes the pawl to move a single tooth along the ratchet wheel.

In some embodiments, the pawl includes an elongate aperture configured to fit around a portion of the plurality of teeth of the ratchet wheel.

In some embodiments, a spring is mechanically linked to the actuator lever and wherein the spring is configured to aid in returning the actuator lever to an original position following actuation of the shape memory wire.

In some embodiments, the syringe assembly comprises a drive tube having internal threads interfaced with a lead screw attached to the plunger and the ratchet wheel is disposed around the drive tube such that rotation of the ratchet causes rotation of the drive tube and lead screw to advance the plunger.

In some embodiments, the actuator lever pivots about a pin.

In some embodiments, an adhesive patch is configured to retain the ambulatory infusion pump on a user's body.

In embodiments, an ambulatory infusion pump can include a reservoir configured to contain a medicament, a syringe assembly including a plunger configured to dispense medicament from the reservoir and a ratchet wheel and pawl mechanism mechanically linked to the syringe assembly. A shape memory wire can be mechanically linked with the ratchet and pawl mechanism such that actuation of the shape memory wire shortens the shape memory wire to cause the shape memory wire to move the pawl to rotate the ratchet wheel and syringe assembly to cause the plunger to dispense a predetermined amount of medicament from the reservoir.

In some embodiments, the pawl pulls on the ratchet wheel when the shape memory wire is actuated.

In some embodiments, the pawl pushes the ratchet wheel when the shape memory wire is actuated.

In some embodiments, the ratchet wheel comprises a plurality of teeth and wherein a distance between each tooth corresponds to the predetermined amount of medicament.

In some embodiments, each actuation of the shape memory wire causes the pawl to move a single tooth along the ratchet wheel.

In some embodiments, the pawl includes an elongate aperture configured to fit around a portion of the plurality of teeth of the ratchet wheel.

In some embodiments, an actuator lever is configured to cause a corresponding movement of the pawl when moved by the shape memory wire, and a spring mechanically is linked to the actuator lever to aid in returning the actuator lever to an original position following actuation of the shape memory wire.

In some embodiments, the actuator lever pivots about a pin.

In some embodiments, the syringe assembly comprises a drive tube having internal threads interfaced with a lead screw attached to the plunger and the ratchet wheel is disposed around the drive tube such that rotation of the ratchet causes rotation of the drive tube and lead screw to advance the plunger.

In some embodiments, an adhesive patch is configured to retain the ambulatory infusion pump on a user's body.

Embodiments of the present disclosure include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718;

9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; 10,569,016; 10,736,037; 10,888,655; 10,994,077; 11,116,901; 11,224,693; 11,291,763; 11,305,057; 11,458,246; and 11,464,908 and commonly owned U.S. Patent Publication Nos. 2009/0287180; 2012/0123230; 2013/0053816; 2014/0276423; 2014/0276569; 2014/0276570; 2018/0071454; 2019/0307952; 2020/0206420; 2020/0329433; 2020/0368430; 2020/0372995; 2021/0001044; 2021/0113766; 2021/0154405; 2021/0353857; 2022/0062553; 2022/0139522; 2022/0223250; 2022/0233772; 2022/0233773; 2022/0238201; 2022/0265927; 2022/0344017; and 2022/0370708 and commonly owned U.S. patent application Ser. Nos. 17/368,968; 17/732,208; 17/878,681; 17/879,959; 17/886,998; 17/896,492; 17/961,206; 17/964,513; 18/011,060; 18/071,814; 18/071,835; and Ser. No. 18/075,029.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump, comprising:
- a reservoir configured to contain a medicament;
- a syringe assembly including a plunger configured to dispense medicament from the reservoir;
- a ratchet wheel configured to rotate the syringe assembly, the ratchet wheel comprising a plurality of teeth extending around an outer circumferential surface of the ratchet wheel;
- a pawl configured to engage with the plurality of teeth of the ratchet wheel, wherein the pawl includes an elongate aperture configured to fit around a portion of the plurality of teeth of the ratchet wheel;
- an actuator lever mechanically linked to the pawl; and
- a shape memory wire mechanically linked with the actuator lever, wherein actuation of the shape memory wire shortens the shape memory wire to cause the shape memory wire to move the actuator lever such that the actuator lever moves the pawl to rotate the ratchet wheel and syringe assembly to cause the plunger to dispense a predetermined amount of medicament from the reservoir.

2. The ambulatory infusion pump of claim 1, where the actuator lever pulls on the pawl to rotate the ratchet wheel and syringe assembly when the shape memory wire is actuated.

3. The ambulatory infusion pump of claim 1, wherein the actuator lever pushes on the pawl to rotate the ratchet wheel and syringe assembly when the shape memory wire is actuated.

4. The ambulatory infusion pump of claim 1, wherein a distance between each tooth corresponds to the predetermined amount of medicament.

5. The ambulatory infusion pump of claim 1, wherein each actuation of the shape memory wire causes the pawl to move a single tooth along the ratchet wheel.

6. The ambulatory infusion pump of claim 1, further comprising a spring mechanically linked to the actuator lever and wherein the spring is configured to aid in returning the actuator lever to an original position following actuation of the shape memory wire.

7. The ambulatory infusion pump of claim 1, wherein the syringe assembly comprises a drive tube having internal threads interfaced with a lead screw attached to the plunger and wherein the ratchet wheel is disposed around the drive tube such that rotation of the ratchet wheel causes rotation of the drive tube and lead screw to advance the plunger.

8. The ambulatory infusion pump of claim 1, wherein the actuator lever pivots about a pin.

9. The ambulatory infusion pump of claim 1, further comprising an adhesive patch configured to retain the ambulatory infusion pump on a user's body.

10. The ambulatory infusion pump of claim 1, wherein the pawl pushes the ratchet wheel when the shape memory wire is actuated.

11. An ambulatory infusion pump, comprising:
- a reservoir configured to contain a medicament;
- a syringe assembly including a plunger configured to dispense medicament from the reservoir;
- a ratchet wheel and pawl linked to the syringe assembly, the pawl comprising an elongate lever configured to interface with an outer circumferential surface of the ratchet wheel; and
- a shape memory wire mechanically linked with the ratchet wheel and pawl, wherein actuation of the shape memory wire shortens the shape memory wire to cause the shape memory wire to move the pawl to rotate the ratchet wheel and syringe assembly to cause the plunger to dispense a predetermined amount of medicament from the reservoir,
- wherein the syringe assembly comprises a drive tube having internal threads interfaced with a lead screw attached to the plunger and wherein the ratchet wheel is disposed around the drive tube such that rotation of the ratchet wheel causes rotation of the drive tube and lead screw to advance the plunger.

12. The ambulatory infusion pump of claim 11, wherein the pawl pulls on the ratchet wheel when the shape memory wire is actuated.

13. The ambulatory infusion pump of claim 11, wherein the ratchet wheel comprises a plurality of teeth and wherein a distance between each tooth corresponds to the predetermined amount of medicament.

14. The ambulatory infusion pump of claim 13, wherein each actuation of the shape memory wire causes the pawl to move a single tooth along the ratchet wheel.

15. The ambulatory infusion pump of claim 13, wherein the pawl includes an elongate aperture configured to fit around a portion of the plurality of teeth of the ratchet wheel.

16. The ambulatory infusion pump of claim 11, further comprising an actuator lever configured to cause a corresponding movement of the pawl when moved by the shape memory wire, and a spring mechanically linked to the actuator lever to aid in returning the actuator lever to an original position following actuation of the shape memory wire.

17. The ambulatory infusion pump of claim 16, wherein the actuator lever pivots about a pin.

18. The ambulatory infusion pump of claim 11, further comprising an adhesive patch configured to retain the ambulatory infusion pump on a user's body.

19. An ambulatory infusion pump, comprising:

a reservoir configured to contain a medicament;

a syringe assembly including a plunger configured to dispense medicament from the reservoir;

a ratchet wheel and pawl mechanically linked to the syringe assembly, the pawl comprising an elongate lever configured to interface with an outer circumferential surface of the ratchet wheel; and a shape memory wire mechanically linked with the ratchet wheel and pawl, wherein actuation of the shape memory wire shortens the shape memory wire to cause the shape memory wire to move the pawl to rotate the ratchet wheel and syringe assembly to cause the plunger to dispense a predetermined amount of medicament from the reservoir, wherein the pawl pushes the ratchet wheel when the shape memory wire is actuated.

20. The ambulatory infusion pump of claim 19, wherein the syringe assembly comprises a drive tube having internal threads interfaced with a lead screw attached to the plunger and wherein the ratchet wheel is disposed around the drive tube such that rotation of the ratchet wheel causes rotation of the drive tube and lead screw to advance the plunger.

* * * * *